United States Patent [19]
Kessler et al.

[11] Patent Number: 5,645,061
[45] Date of Patent: Jul. 8, 1997

[54] PROCESS AND DEVICE FOR THE DETERMINATION OF LOCAL DYE CONCENTRATION AND OF SCATTERING PARAMETERS IN ANIMAL AND HUMAN TISSUES

[76] Inventors: Manfred Kessler, Schlehenstr. 14; Klaus Frank, Schlehenstr. 14A, both of D-8520 Erlangen, Germany

[21] Appl. No.: 299,816

[22] Filed: Sep. 1, 1994

Related U.S. Application Data

[60] Continuation of Ser. No. 178,670, Jan. 7, 1994, abandoned, which is a division of Ser. No. 801,618, Dec. 2, 1991, Pat. No. 5,284,137, which is a continuation-in-part of Ser. No. 385,617, Jul. 26, 1989, abandoned.

[30] Foreign Application Priority Data

Jul. 26, 1988 [DE] Germany .......................... 38 25 352.6

[51] Int. Cl.⁶ ...................................................... A61B 1/07
[52] U.S. Cl. .......................... 128/634; 128/664; 128/774; 128/897; 356/337; 600/118
[58] Field of Search ...................................... 128/4-6, 633, 128/634, 664, 665, 774, 897, 898; 607/88; 356/335, 336, 337, 342; 600/117, 118

[56] References Cited

U.S. PATENT DOCUMENTS

| | | | |
|---|---|---|---|
| 3,653,767 | 4/1972 | Liskowity | 356/336 |
| 3,830,568 | 8/1974 | Allen . | |
| 3,916,197 | 10/1975 | Fulwyler | 356/335 |
| 4,178,917 | 12/1979 | Shapiro . | |
| 4,321,930 | 3/1982 | Jöbsis et al. . | |
| 4,497,577 | 2/1985 | Sato et al. | 356/336 |
| 4,702,229 | 10/1987 | Zobel | 128/4 |
| 4,718,417 | 1/1988 | Kittrell et al. | 606/7 |
| 4,801,205 | 1/1989 | Tatsuno . | |

FOREIGN PATENT DOCUMENTS

| | | |
|---|---|---|
| 0047094 | 3/1982 | European Pat. Off. . |
| 0063778 | 7/1986 | European Pat. Off. . |
| 3003941 | 8/1980 | Germany . |
| 3019234 | 12/1981 | Germany . |

OTHER PUBLICATIONS

"Continuous, Non-Invasive Measurements of Arterial Blood Oxygen Levels" by Merrick et al; Hewlett Packard Journal; vol. 28, No 2, pp 2–10; Jan. 1989.

*Primary Examiner*—David M. Shay
*Attorney, Agent, or Firm*—Matthew C. Rainey; Vincent M. Powers

[57] ABSTRACT

A device for determining size variations of tissue particles. The device includes a light source and an illuminating light guide capable of irradiating light into a human tissue to produce back-scattered light, and at least two receiving light guides at different radial distances from the illuminating light guide, for receiving back-scattered light from the tissue. The device can be used for determining size variations of tissue particles such as mitochondria.

3 Claims, 11 Drawing Sheets

| PARTICLE SIZE 2r (μm) | 0.1 | 0.15 | 0.3 | 0.6 | 2 |
|---|---|---|---|---|---|
| RELATIVE SIZE X | 1.0 | 1.5 | 3.0 | 6.0 | 20.0 |
| RELATIVE REFRACTIVE INDEX m | 1.5 | 1.5 | 1.5 | 1.5 | 1.5 |
| WAVELENGTH λ (nm) | 500 | 500 | 500 | 500 | 500 |
| RELATIVE FORWARD SCATTERED LIGHT INTENSITY $I_F$ | 0.245 | 3.19 | 82 | 1620 | 85146 |
| RELATIVE BACK-SCATTERED LIGHT INTENSITY $I_B$ | 0.039 | 0.15 | 0.4 | 50.2 | 599 |
| RATIO $I_F / I_B$ | 2.635 | 11.11 | 20.5 | 32.3 | 142 |

PROCESS AND DEVICE FOR THE DETERMINATION OF LOCAL DYE CONCENTRATION AND OF SCATTERING PARAMETERS IN ANIMAL AND HUMAN TISSUES

This is a continuation of application Ser. No. 08/178,670, filed Jan. 7, 1994, which is a divisional of application Ser. No. 07/801,618, filed Dec. 12, 1991, now U.S. Pat. No. 5,284,137, which is a continuation of application Ser. No. 07/385,617, which was filed Jul. 26, 1989, now abandoned.

BACKGROUND AND SUMMARY OF THE INVENTION

The invention relates to a process for the determination of local dye concentrations in animal and human tissues, in which light of differing wavelengths is irradiated into a subregion of the tissue, at least a part of the back-scattered light is collected, the diffuse reflectance (remission) is determined as a function of the wavelength and the concentration of dyes is determined from the spectral diffuse reflectance.

Such a process is known, for example, from the dissertation "Bestimmung von Hamoglobin—Oxygenierung und relativer Hamoglobin—Konzentration in biologischen Systemen durch Auswertung von Remissionsspektren mit Hilfe der Kubelka-Munk-Theorie" ("Determination of hemoglobin oxygenation and relative hemoglobin concentration in biological systems by evaluation of diffuse reflectance spectra by means of the Kubelka-Munk theory") by Wolfgang D ümmler, Erlangen, 1988.

The term "local" concentration is to be understood here especially and exemplarily as the intracapillary region.

The term "dyes" is to be understood as dyes intrinsic to tissues (pigments), especially hemoglobin, but also cytochromes and supplied dyes, for which the elution kinetics is then investigated.

"Light of differing wavelengths" is generally the mixed light of a lamp (e.g., a xenon high-pressure lamp), but can also be, for example, the light of a tunable laser light source. The light is usually spectrally decomposed only after the diffuse reflection, and the intensity is evaluated as a function of the wavelength, the spectrally differing initial intensities being taken into consideration computationally.

The term "subregion" is to be understood as a region with relatively small surface area, typically in the range of 50–100 μm diameter. The depth extent in the tissue depends on numerous factors and is on the order of 150 μm (falloff to l/e). As is described further below, however, the tissue volume from which the diffuse reflectance is obtained is both tissue-specific and equipment-specific and also depends on the hemoglobin concentration.

As is described in detail in the cited dissertation by D ümmler, the absolute measurement of the hemoglobin concentration, for example, is affected by considerable difficulties. Therefore, the invention creates a process and a device which makes it possible to determine substantially more exactly the dye concentration and other scattering factors in the tissue, especially the hemoglobin absolute concentration.

This is achieved according to the invention in that, in one step, radiation from a first wavelength region in which the influence of the hemoglobin on the diffuse reflectance is small is irradiated and the diffuse reflectance in this wavelength region is determined, that in a separate step light from a second wavelength region in which the diffuse reflectance is dominated by the influence of the hemoglobin is irradiated into the same subregion of the tissue and the diffuse reflectance in this wavelength region is determined, that from the diffuse reflectance in the first wavelength region and at least one tissue-type-specific standard basic diffuse reflectance curve obtained in advance for both wavelength regions a tissue-person-specific standard basic diffuse reflectance curve for the second wavelength region is determined, and that from the determined tissue-person-specific standard basic diffuse reflectance curve and the measured diffuse reflectance in the second wavelength region a value for the hemoglobin concentration is obtained.

The classification of the steps, e.g., as is to be found from the numbering in the claims, is done systematically. Digits after a colon are to signify alternatives of the step indicated in the first digit; following digits without a colon are substeps of a main step. The light measurements in the two wavelength regions I and II, 1.1. and 1.2., are systematically different (sub)steps but in practice occur simultaneously, the order being of no significance. The basic measurements (0. steps) generally occur before ("in advance of") the actual measurements, but in principle can also be performed subsequently, since the actual measurement values can also be stored.

The term "basic diffuse reflectance" is understood here as the diffuse reflectance of the hemoglobin-free tissue, as can be found for example with a hemoglobin-free perfusion of the tissue.

The term "tissue-type-specific" is understood as the special features which result from the special nature of the tissue (e.g., rat liver or human skin). The term "tissue-person-specific" designates values and curves in which the actual measurement of at least one of the two diffuse reflectance curves is already incorporated, even if that be only through the influence of the measurement on the choice from a family of curves determined in advance.

The solution according to the invention has the specific advantage that, owing to the fact that in the first wavelength region where the hemoglobin has a window the basic diffuse reflectance is recognizable in comparatively unperturbed form, the influence of the basic diffuse reflectance in the second wavelength region where it is generally completely covered over by the hemoglobin influence can also be more exactly estimated and correspondingly eliminated. The more exact value thus obtained can be further refined in further process steps.

Preferably, a family of tissue-type-specific standard basic diffuse reflectance curves is obtained in advance from tissue samples of the same tissue type, and the measured diffuse reflectance curve in the first wavelength region is assigned to the closest matching branch in the first wavelength region from the family of standard basic diffuse reflectance curves, and the associated branch of this standard basic diffuse reflectance curve in the second wavelength region is selected as the tissue-person-specific standard basic diffuse reflectance curve.

Standard basic diffuse reflectance curves are understood as basic diffuse reflectance curves that were measured and stored "in advance" from a large number of tissues of the tissue type to be measured, e.g., by means of hemoglobin-free perfusion. In this embodiment of the invention, curves are determined which as a family of curves cover a large range of diffuse reflectances at one wavelength without the individual curves intersecting. From the family the curve is then selected which comes closest to the measured curve in the first wavelength region, and the other branch of this selected (tissue-type-specific) standard basic diffuse reflectance curve in the second wavelength region becomes the tissue-person-specific (standard) basic diffuse reflectance curve there. This has the special advantage that after such a family of curves is prepared it becomes possible in a simple manner to infer the (in itself unknown) behavior in the second wavelength region of the curve measured in the first wavelength region.

In an especially preferred embodiment, the assignment of a standard basic diffuse reflectance curve from the family of standard basic diffuse reflectance curves obtained in advance in the first wavelength region to the measured diffuse reflectance curve is accomplished in that the standard basic diffuse reflectance curve with the value at a predetermined isosbestic wavelength in the first wavelength region which is equal to or closest to the measured diffuse reflectance value at that isosbestic wavelength is selected, and the value of the selected standard basic diffuse reflectance curve at a predetermined isosbestic wavelength in the second wavelength region is used as the value for the determination of the hemoglobin concentration.

The values at the isosbestic wavelengths are taken because no additional error occurs there due to the (likewise still unknown) oxygenation of the hemoglobin. But these values also suffice for the stated purpose because the diffuse reflectance value from the diffuse reflectance curve at an isosbestic wavelength, corrected by the basic diffuse reflectance, already suffices to determine the concentration from the diffuse reflectance value using a suitably calibrated device.

In an alternatively preferred embodiment, an averaged tissue-type-specific standard basic diffuse reflectance curve is obtained in advance from tissue samples of the same tissue type, and the measured diffuse reflectance curve in the first wavelength region is compared by ratio to the averaged standard basic diffuse reflectance curve, and, from the ratio obtained and the part of the tissue-type-specific averaged standard basic diffuse reflectance curve in the second wavelength region, a tissue-person-specific standard basic diffuse reflectance curve in the second wavelength region is obtained.

Thus, in distinction to the previous alternative, now one typical curve is determined from a plurality of advance measurements of the basic diffuse reflectance of the tissue (e.g., by hemoglobin-free perfusion) over both wavelength regions, which for that reason is also designated as the "averaged" standard basic diffuse reflectance curve (although the curves of the family of curves may in turn also have resulted from averagings).

"Comparison by ratio" is to be understood in any case not only as the formation of a mathematical ratio, but rather numerous methods are conceivable by which from the deviations of the behavior of the measured diffuse reflectance curve in the first wavelength region from the behavior of the averaged standard diffuse reflectance curve in the first wavelength region via the behavior of the averaged standard diffuse reflectance curve in the second wavelength region it is possible to infer the imaginary continuation of the measured curve (considered as the basic diffuse reflectance curve in zeroth approximation) as the tissue-person-specific basic diffuse reflectance curve in the second wavelength region.

In an especially preferred embodiment, the comparison by ratio of the averaged standard basic diffuse reflectance curve in the first wavelength region to the measured diffuse reflectance curve (in the first wavelength region) is accomplished in that the value of the averaged standard basic diffuse reflectance curve in the first wavelength region at a predetermined isosbestic wavelength in the first wavelength region is compared by ratio to the measured value of diffuse reflectance at that isosbestic wavelength, and by means of the obtained ratio the value of the averaged standard basic diffuse reflectance curve at a predetermined isosbestic wavelength in the second wavelength region is used to obtain a value of diffuse reflectance at that isosbestic wavelength, which is used as the value for the determination of the hemoglobin concentration.

The advantage of the use of the values at isosbestic wavelengths was already explained. The diffuse reflectance value, which allows the hemoglobin concentration to be inferred, is generally determined by subtracting the value obtained at the isosbestic wavelength in the second wavelength region from the measured value of diffuse reflectance at that wavelength.

In another preferred embodiment, in a continuation of the process, the measured curve in the first wavelength region is corrected by means of the value obtained for the hemoglobin concentration, whereby a second, improved approximation is obtained for the tissue-person-specific basic diffuse reflectance in the first wavelength region.

In the above process, the measured diffuse reflectance curve in the first wavelength region, which still contained the influence (which of course is small there) of the hemoglobin concentration, was a "zeroth other approximation" of a tissue-person-specific basic diffuse reflectance curve in the first wavelength region. This zeroth other approximation can now be improved by eliminating the hemoglobin concentration (which in turn is known in first approximation from the above process steps) from the curve. The further approximation thus obtained is advantageously incorporated into the above-described process steps in place of the measured diffuse reflectance curve.

Thus, in an especially preferred embodiment, steps 2 to 4 (vide infra) are performed with the improved curve instead of the measured diffuse reflectance curve, whereby a better approximation value is obtained for the hemoglobin concentration and a further improved curve is obtained as tissue-person-specific basic diffuse reflectance in the first wavelength region.

In a preferred manner, the above steps 2. to 4. are repeated multiple times, using the improved values and curves as a basis in each instance.

The region from 630 nm to 1000 nm is preferred as a wider first wavelength region.

The region from 750 nm to 850 nm is preferred as a narrower first wavelength region. Hemoglobin has a window in these regions, i.e., its influence on the diffuse reflectance is small.

The region from 500 nm to 620 nm is preferred as a wider second wavelength region.

The region from 550 nm to 570 nm is preferred as a narrower second wavelength region. In the latter two regions, the influence of hemoglobin on the basic diffuse reflectance is large.

The invention also relates to a process for the determination of the oxygenation of hemoglobin, especially using one or more of the curves from one or more of the above processes. The determination of the oxygenation of hemoglobin with high accuracy is also of special significance in the monitoring of life processes by means of spectrophotometry.

In this connection, according to the invention, a "pure" hemoglobin curve is obtained from a tissue-person-specific standard basic diffuse reflectance curve and the measured diffuse reflectance curve in the second wavelength region; a family of "pure" hemoglobin curves having been obtained in advance in the range of from 0% to 100% oxygenation by superposition of two pure standard hemoglobin curves, namely for 0% and 100% oxygenation, with different weightings; the "pure" hemoglobin curve, after normalization to 1, is compared to the likewise normalized standard hemoglobin curves of the family, the closest matching one is picked out, and its oxygenation is assumed as the value of the oxygenation for the measured curve.

In an alternatively preferred process for the determination of the oxygenation of hemoglobin, especially using one of the concentration values and especially one of the curves from one of the previously described processes, a two-dimensional family of comparison curves is prepared in advance by means of a plurality of measurements on the same tissue type with hemoglobin of differing concentrations and differing oxygenations, the comparison curves with hemoglobin concentrations in the vicinity of the determined concentration are searched throughout the entire range of oxygenation, and the best matching of the comparison curves yields an assumed value for the oxygenation and an improved value for the concentration.

In this manner, reliable values for important parameters can in turn be obtained simply and quickly with the aid of the measured diffuse reflectance and standard values known in advance.

In a preferred embodiment, the values for the concentration and the oxygenation obtained in the embodiment just described are used in the described step for obtaining an improved tissue-person-specific basic diffuse reflectance curve.

In an especially preferred embodiment, the measured diffuse reflectance curve from the second wavelength region is normalized to the closest matching curve from the above-mentioned two-dimensional family used to determine the oxygenation, the difference between the two curves is plotted versus wavelength and used as a measure of the distortion to determine the penetration depth of the irradiated light, i.e., of the volume V covered by the light.

It has turned out that this distortion can be used as a measure of the penetration depth. Corresponding distortion, curves determined in advance are stored, the corresponding volume is assigned to them, and then the distortion curve obtained by the comparison is assigned to the closest matching curve from the stored distortion curves and thus the volume is determined.

In an especially preferred embodiment, the Erlanger light-guide microspectrophotometer (Erlanger Mikrolichtleiterspektrophotometer (EMPHO)) is used for the above measurements. It is described in more detail further below. The graded-density interference filter disk used in it covers preferably both the first wavelength region and also the second wavelength region. In that way, the measured diffuse reflectance curves of the first and second wavelength regions can be obtained in one rotation of the disk.

In a preferred embodiment, the light-guide microspectrophotometer has means for absolute calibration of the illuminating and detecting system. The absolute calibration is especially important because the measurements made in advance, which should be made with the same device or must be convened in a device-specific manner, must occur under defined conditions comparable to those of the actual measurement. In particular, such means are a white standard and a standard light source, which are explained below.

The invention relates also to a device for the determination of size variations of tissue particles. The observation of such variations, e.g., of the size change of mitochondria, is of special practical importance because it makes it possible, for example, to detect a cerebral edema at an early stage. This is accomplished by means of a device with an illuminating light guide which radiates light into the tissue, at least two receiving light guides at different radial distances from the illuminating light guide which receive the back-scattered light and which preferably are disposed along a line on both sides of the illuminating light guide, and an evaluation unit for each of the light guides which determines and evaluates the time variation of the back-scattered intensity relative to the other light guides.

Such an evaluation unit can be built analogously to the Erlanger light-guide microspectrophotometer. A flattening or other deformation of the back-scattering characteristic can then be recognized, which in turn allows one to infer the variation of the particle size.

DESCRIPTION OF THE DRAWINGS

In the following the invention is explained in more detail by means of preferred exemplary embodiments with reference to the appended drawings, to which express reference is made owing to their clarity and ease of understanding with respect to the disclosure.

They show:

FIG. 10: A table by means of which the variation of the back-scattering can be seen as a function of the particle size (back-scattering angle=180°);

DETAILED DESCRIPTION OF THE PREFERRED EMBODIMENTS

Figure 1:
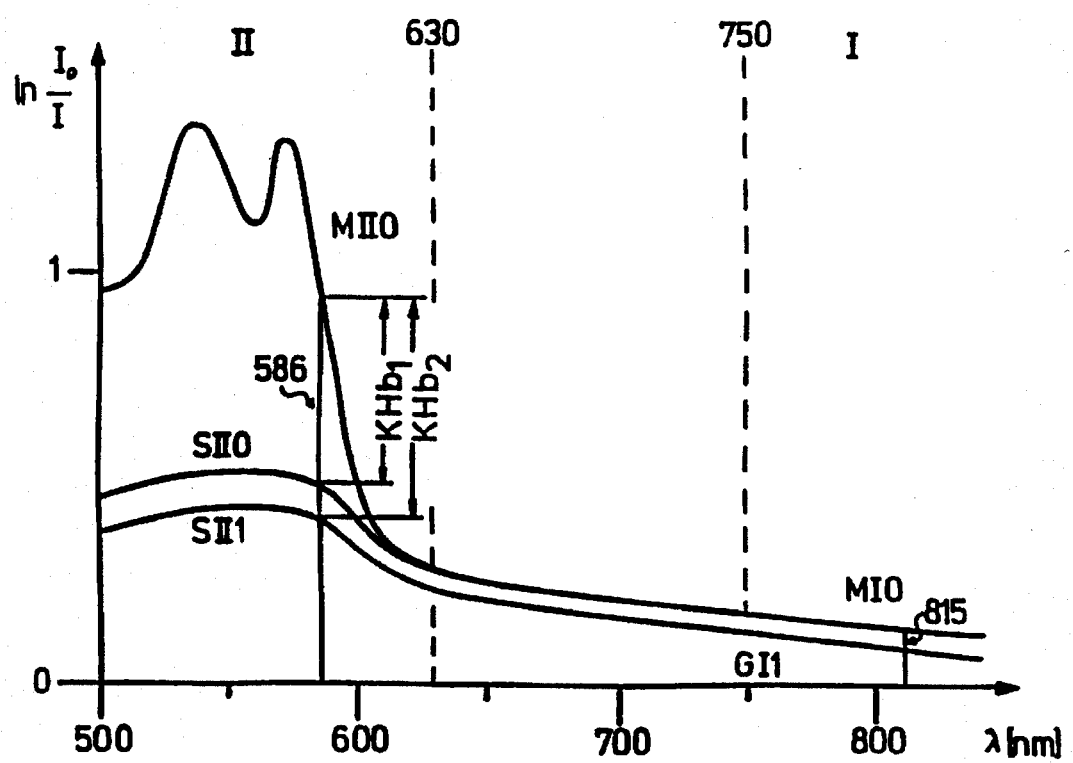
FIG. 1: A typical diffuse reflectance curve MI0 in the wavelength region I, measured on rat livers and already corrected to white incident radiation, as well as the same curve after allowing for the hemoglobin concentration in first approximation, GI1; and in the wavelength region II a measured diffuse reflectance curve MII0, measured practically simultaneously with the curve MI0, as well as the standard basic diffuse reflectance curve SII0 belonging to the curve MI0.

FIG. 1 shows on the right a first measured curve MI0 (M is to indicate "measured", I is to indicate the wavelength region I (here 750–850 nm), and the digit 0 indicates that it involves a curve which can be considered as the zeroth order approximation of the basic diffuse reflectance curve). Ln $I_0/I$ is used here as a measure of the diffuse reflectance. The curve was measured on rat livers with an Erlanger light-guide microspectrophotometer, which is explained in more detail in, among other places, the dissertation "Optische Streuung an biologischen Partikeln und Zellen" ("Optical scattering from biological particles and cells"), Erlangen 1985, by one of the inventors, Frank, but also hereinbelow.

The curve exhibits only a slight influence of the hemoglobin, since hemoglobin has a window (i.e., is virtually transparent) in region I.

The term "basic diffuse reflectance" is understood here as the diffuse reflectance of the hemoglobin-free tissue, as can be found, for example, for a hemoglobin-free perfusion of the tissue. This basic diffuse reflectance is still tissue-type-specific, depends on the redox state of the remaining cell pigments and possibly added dyes, and is also still tissue-person-specific, although only to a slight extent. Accordingly, it is necessary to determine the actual "true" basic diffuse reflectance as exactly as possible in order to be able to determine the concentrations, oxygenation and redox state of different pigments and dyes.

The measured curve MI0 (systematically considered in a process step 1.1) represents an approximation (zeroth order) in the process, because it is still dependent on the influence (which in the selected wavelength region I from 750 to 850 nm is of course small) of the hemoglobin concentration (KHb) and of the oxygenation ($HbO_2/Hb$).

In another step (2.), a corresponding standard basic diffuse reflectance curve in the wavelength region II is selected for the measured basic diffuse reflectance curve MI0.

For the determination of the so-called "standard" basic diffuse reflectance curves (that is, a 0th process step), a large number (about 100) of in-vivo and in-vitro samples which have undergone hemoglobin-free perfusion are used to determine which diffuse reflectance curves result in region II for particular diffuse reflectances in region I. Thus, a large number of families of values is determined, and the families of values contain values of a curve for the different wavelengths from wavelength regions I and II.

In the actual table (FIG. 4), a sequence at an isosbestic point of the hemoglobin in region II is uniquely assigned to a sequence (one value each from the families of values forming a curve) of diffuse reflectances at an (here "the") isosbestic wavelength of the hemoglobin in wavelength region I (in such a way that the values of the value pair lie on the same standard basic diffuse reflectance curve). Thus, the table represents a narrowest section from the associated curves at the indicated wavelengths.

The isosbestic wavelength of the hemoglobin (815 nm) was selected in wavelength region I, since the influence of the oxygenation of the hemoglobin on the diffuse reflectance in wavelength region I also is greater than the influence of the oxidation of the cytochromes, which latter influence changes appreciably only at an oxygen partial pressure of less than 5 torr. The choice of the isosbestic wavelength results in independence from the (in this step still unknown) oxygenation of the hemoglobin. The error of the zeroth order approximation, the measured curve MI0, depends there only on the concentration of the hemoglobin.

Thus, for the assignment of a standard basic diffuse reflectance curve (SII0) of zeroth order approximation in wavelength region II, the value of the sequence at the isosbestic wavelength in wavelength region I is selected which is equal to or closest to the measured value at the isosbestic wavelength on the curve MI0, and by means of Table 2 there is assigned to the latter the associated value of the sequence in wavelength region II and thus also the entire branch of the corresponding standard basic diffuse reflectance curve in II.

Alternatively, in a process step 0.2 a single "averaged standard basic diffuse reflectance curve" averaged from all measured standard basic diffuse reflectances is formed, and, for the differences (or factors) in comparison to other diffuse reflectances at the isosbestic wavelength in region I, tables are produced (using a large number of standard basic diffuse reflectance curves covering both wavelength regions) which assign to a difference (or a factor) a difference (or a factor) at wavelengths in the 2nd wavelength region, especially again at an isosbestic wavelength therein. Then, in the second process step, alternatively (step 2.2) the difference (or the ratio) between the diffuse reflectance of the measured curve MI0 and the averaged standard basic diffuse reflectance curve at the isosbestic wavelength is found, and the averaged standard basic diffuse reflectance curve in the second wavelength region at the isosbestic wavelength is loaded with the associated factor or summand on the basis of the table so as to obtain a curve, or at least its value at an isosbestic wavelength in wavelength region II, which represents the 0th approximation of the (standard) basic diffuse reflectance in the second wavelength region II, SII0.

An isosbestic wavelength is also selected in region II (specifically 586 nm in the exemplary embodiment) so as to be independent of the unknown level of oxygenation.

Figure 2:
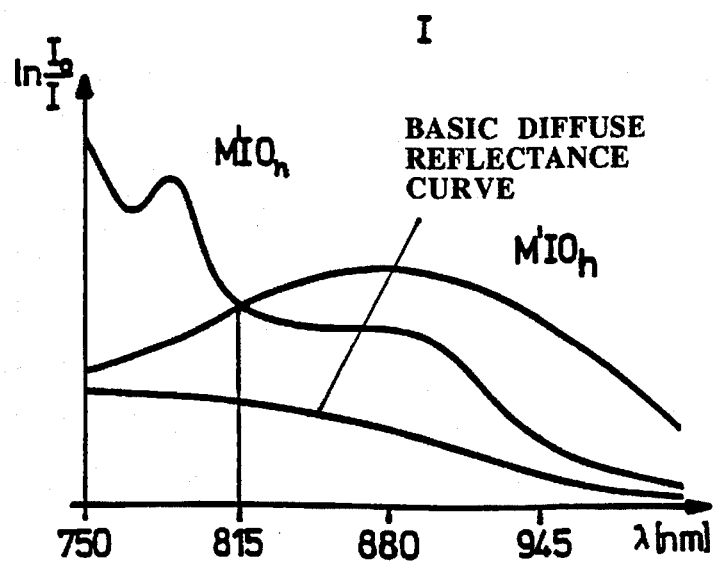
FIG. 2: The curves corresponding to the curve MI0 at higher ($M'I0_h$) and lower ($M'I0_n$) hemoglobin oxygenation; as well as an associated basic diffuse reflectance curve.

FIG. 1 shows in the left half a measured diffuse reflectance curve at the same tissue location (systematically considered in a step 1.2.), obtained in the same passage of an interference graded-density filter disk (see below, FIG. 13). It is designated as MII0 as the measured curve in wavelength region II and is a zeroth order approximation. Also drawn to the left in FIG. 1 is the standard basic diffuse reflectance curve SII0 belonging to the measurement value determined in the first wavelength region I, which also as described above is present as a table (a section of which is shown in FIG. 2) or is determined from the comparison of the averaged standard basic diffuse reflectance curve in region I with the curve MI0, as alternatively described above. At the isosbestic wavelength, from the measured total diffuse reflectance (curve MIII0), which is composed of the basic diffuse reflectance (represented in zeroth order approximation by the standard basic diffuse reflectance) and the hemoglobin-dependent diffuse reflectance, by subtraction of the value of the standard basic diffuse reflectance curve SII0 at the actual isosbestic wavelength (586 nm) from the value of the measured diffuse reflectance curve MIII0, the hemoglobin diffuse reflectance and thus a measure for the hemoglobin concentration in first order approximation, KHb1, is obtained (in step 3.). Thus, a first approximation value, KHb1, for the hemoglobin concentration is obtained.

This concentration value KHb1 is used to correct the measured curve in region I, MI0, and one obtains for the basic diffuse reflectance a corresponding better curve of first approximation, GI1, by subtracting from MI0 (in a step 4.) the (additional) amplitude value produced by the hemoglobin concentration at the isosbestic wavelength of 815 nm at that concentration. The resulting value is used with the table (FIG. 4) (or the alternative process step 2.2) to select a better-matching standard basic diffuse reflectance curve SIII1 (see FIG. 1, left), which in turn serves to improve the value of the hemoglobin concentration to a value KHb2. The latter is used in turn, in the described manner, to determine an improved basic diffuse reflectance curve in region I, GI2. By multiple repetition one can finally obtain a highly improved value for the hemoglobin concentration, KHbn. In another step the oxygenation is determined, possibly with simultaneous improvement of the value for the concentration.

First of all, the standard basic diffuse reflectance curve corresponding to the last iteration stage is subtracted from the measured curve MIII0 to obtain the "pure" hemoglobin curve, HIII0.

By superposition of two pure standard hemoglobin curves, namely for 0% and for 100% oxygenation, with different weighting, a family of "pure" hemoglobin curves is obtained in the range of 0–100% oxygenation.

Then, the corrected measurement curve, HIII0, after normalization to 1, is compared to the likewise normalized curves of this family and the closest matching one is selected (e.g., by the least-squares method).

The degree of oxygenation of the selected curve is assumed as the degree of oxygenation of the measured curve MIII0.

Figure 5:
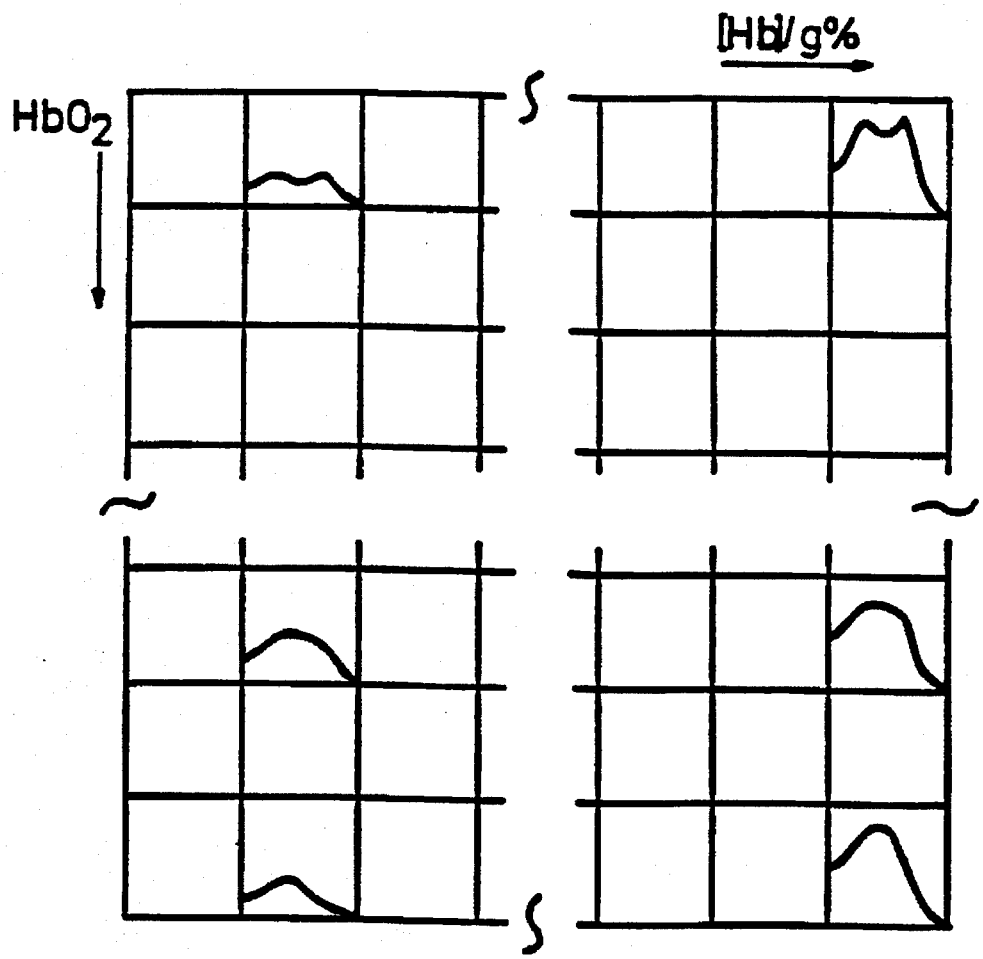
FIG. 5: Schematically, a matrix of values whose fields contain standard hemoglobin spectra of the tissue type of the tissue to be investigated, the rows containing curves with different concentration at the same degree of oxygenation and the columns containing curves with the same concentration at different degrees of oxygenation.

Alternatively, before beginning the actual measurement, standard diffuse reflectance curves were determined with the same device with which the actual measurement is performed, using a very large number of measurements on the same tissue type, which was perfused with hemoglobin of differing concentrations (from 0 to 20%) and differing oxygenations (0 to 100%). The standard diffuse reflectance curves, which in turn are averaged from a large number of measurements for a particular concentration and oxygenation, are arranged in a table or matrix so that, for example, the rows contain the different concentrations at the same oxygenation and the columns contain the different oxygenations at the same concentration. This is illustrated schematically in FIG. 5.

The measured curve MIII0 is now compared with the curves in the table. In an exemplary and preferred manner, the column corresponding to the first approximation of the hemoglobin concentration and one each or in the exemplary embodiment two each of the adjacent columns are searched for all values of the oxygenation.

For the comparison of the curves, in one embodiment of the process the integral of the area under the standard diffuse reflectance curves can be compared with the integral under the measured curve MIII0.

Alternatively, the curves are compared by the least-squares method.

The field of the matrix with the optimally matching curve yields a hemoglobin concentration value, second order approximation, KHb2, and a hemoglobin degree of oxygenation, first order approximation, KHbO$_2$1.

These values are now, for example, used again to get improved values for the basic diffuse reflectance curve and the concentration.

Here also it is evident that the process can be continued until a convergence which is sufficient with respect to the realistic measurement accuracy is reached.

The hemoglobin oxygenation simultaneously allows one to infer the oxidation of the cytochromes. Furthermore, the basic diffuse reflectance curve after subtraction of the hemoglobin influence allows a more exact determination of other parameters in the tissue.

At very low oxygenation, i.e., oxygen partial pressures <5 torr measured in the tissue, other basic diffuse reflectance curves must be used as a basis, but this does not change anything in the basic process.

FIG. 2 shows, at magnified scale, measured curves from wavelength region I corresponding to the curve MI0, one for high hemoglobin oxygenation (M'I0$_h$) and one for low hemoglobin oxygenation (M'I0$_n$).

Figures 3, 4:
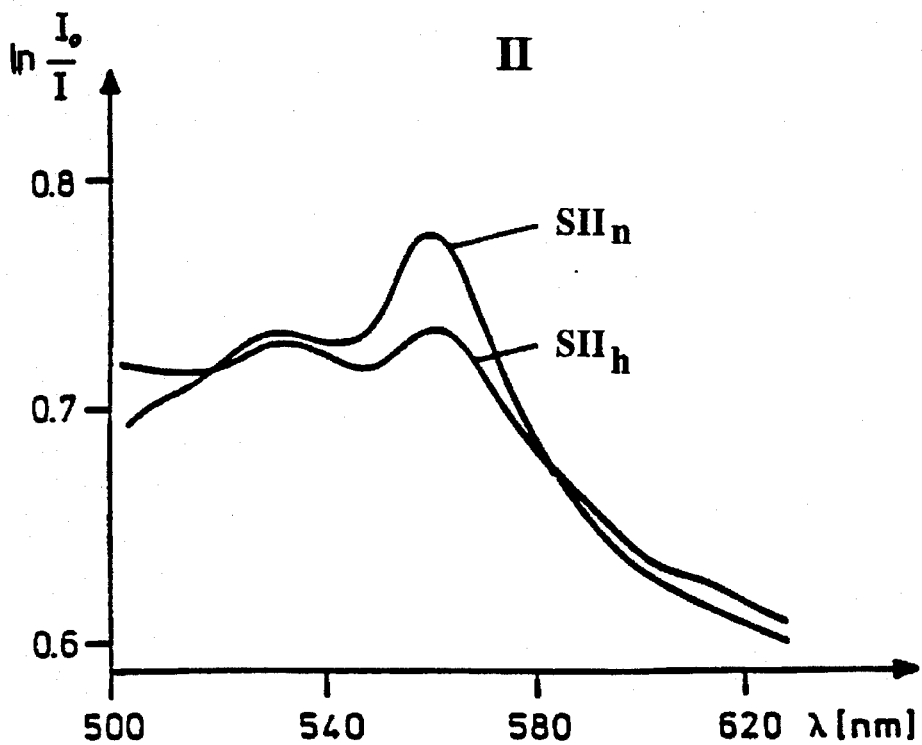
FIG. 3: The standard basic diffuse reflectance curves measured on the perfused rat livers at high ($SII_h$) and low ($SII_n$) oxidation of the respiratory enzymes.
FIG. 4: A matrix of values (excerpt) for the assignment of measured diffuse reflectances at the wavelength λ=815 nm (isosbestic wavelength of hemoglobin in the wavelength region I) to standard basic diffuse reflectance values at λ=586 nm (an isosbestic wavelength in II) in the wavelength region II.

FIG. 3 shows, at magnified scale, standard basic diffuse reflectance curves corresponding to the curves SII, one at high (SII$_h$) and one at low (SII$_n$) oxidation of the respiratory enzymes.

More-exact statements about a "concentration" can only be made by taking into consideration of the tissue (micro) volume covered by the measurement.

The covered volume depends on the following parameters:
1. the utilized wavelength and, very generally, the characteristic of the utilized light source (luminous field density, intensity, stability)
2. the transmission characteristics of the light guide radiating into the tissue (acceptance angle α, length L, diameter d, material)
3. the scattering characteristic of the tissue and the absorption behavior of the dye or dyes
4. the transmission characteristics of the (detecting) light guide receiving the back-scattered light (acceptance angle α, length L, diameter d, material) and of the following detection system
5. the sensitivity of the light-measuring system and/or of the photomultiplier.

Figure 6:
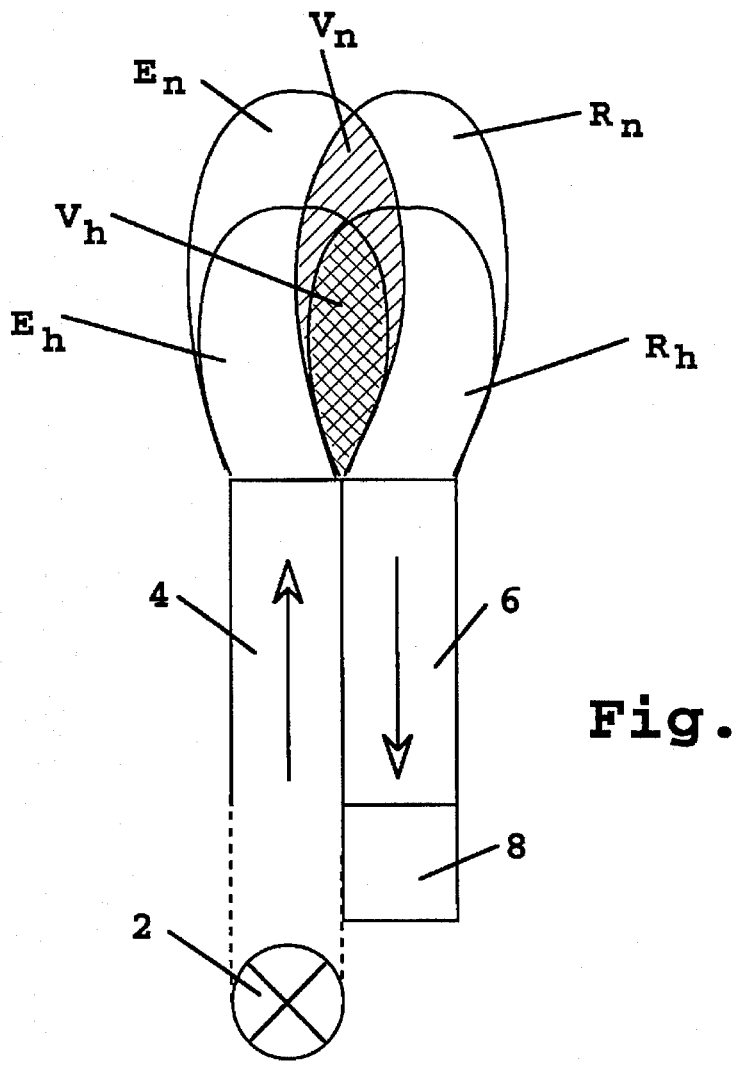
FIG. 6: Schematically, the irradiation by means of a light guide and the detection by means of another light guide, and the volume thereby reached in the tissue.

FIG. 6 shows schematically the illuminating lamp 2, the illuminating light guide 4, the detecting light guide 6 and the photomultiplier 8. The volume into which the illuminating light guide 4 radiates in the tissue is indicated by Eh for a high Hb concentration and by En for a low one; the volume from which the detecting light guide 6 can receive light, taking into consideration the sensitivity of the photomultiplier 8, is designated by $R_h$ and $R_n$, respectively. The intersection volume, $V_h$ and $V_n$ respectively, is the volume on which the concentration measurement is based. A quasi-diffuse illumination is achieved by high luminous density.

It is assumed that the device used to produce the utilized tables (matrices) is the same as that used for the actual measurement, so that to that extent there is no change in the volume or only factors that can be factored out are changed.

Information about the volume covered under certain conditions can also be presented in tabular form. The corresponding values can be obtained by means of measurements on sections of the tissue or in scattering chambers with simulated tissue.

The above-mentioned concentration values are based on volumes which are obtained from the tables as empirical values. However, the volumes can also be corrected by means of a separate procedure.

According to the invention, the distortion of the measured hemoglobin curve MHO compared to the standard diffuse reflectance curve RSII1 determined from the matrix (table) 2 (see FIG. 5) is used as a measure for the penetration depth and thus for the covered volume. For that purpose, the measured hemoglobin curve MHO is normalized to the standard curve determined at the isosbestic wavelength and the difference is plotted versus wavelength.

Figure 7A:
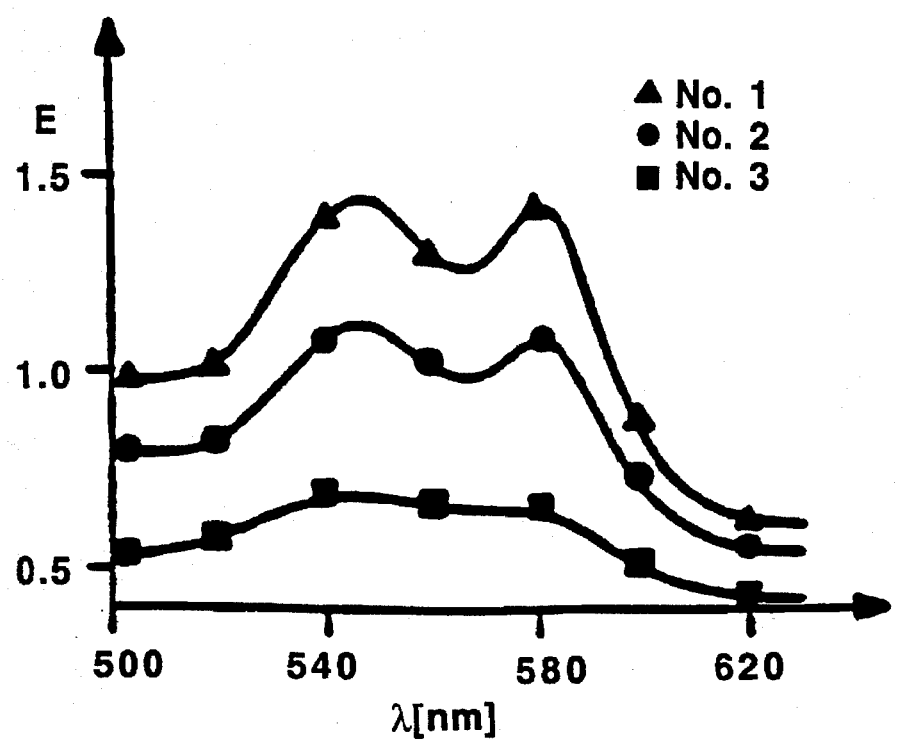
FIGS. 7A-7C: Schematically, three curves which serve to determine the distortion of two measured curves.
Figure 7B:
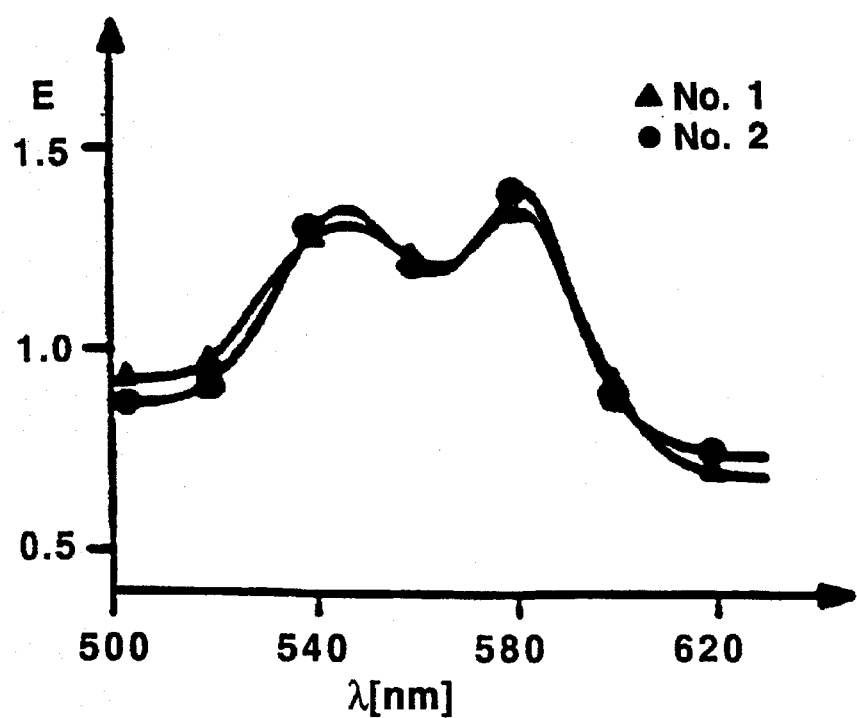
Figure 7C:
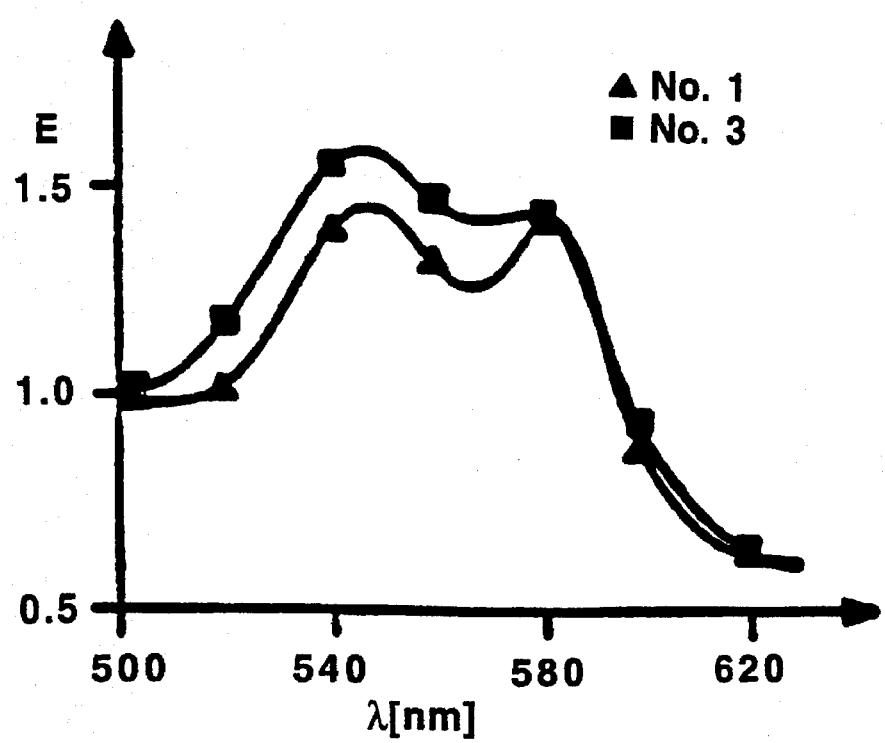
Figure 8:
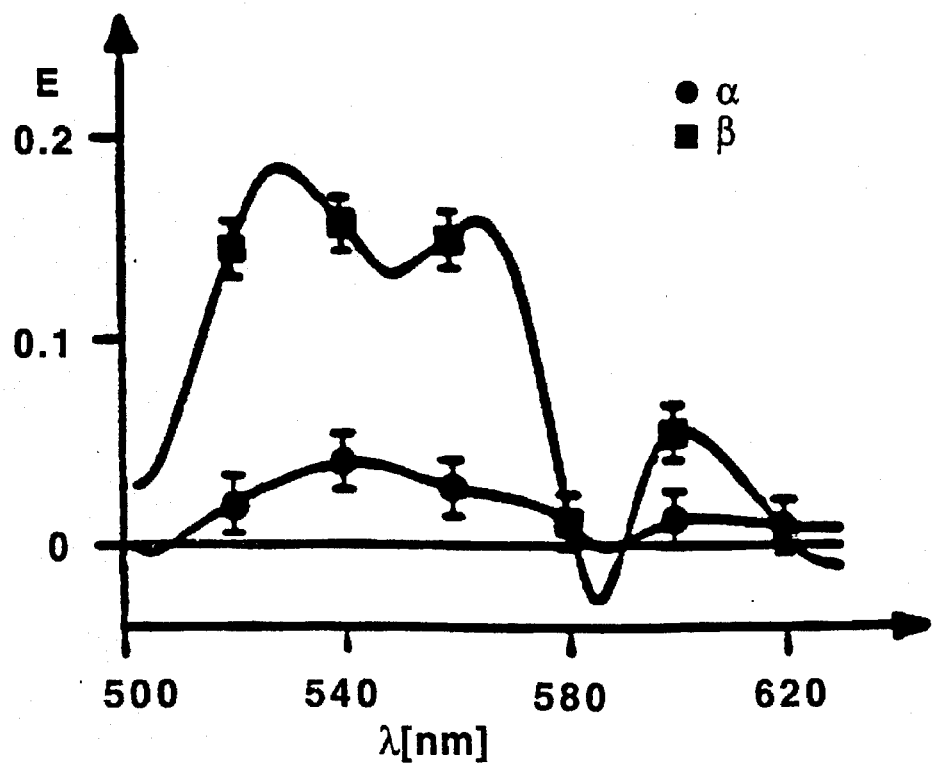
FIG. 8: The difference curves or distortion curves resulting from the curves of FIG. 7.
Figure 11A:
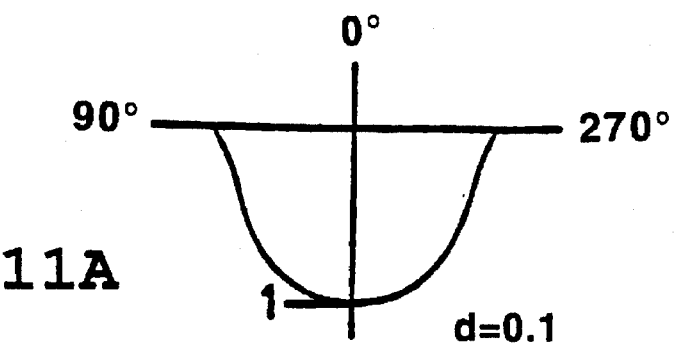
FIG. 11: Angular dependence of back-scattering intensity on particle size.
Figure 11B:
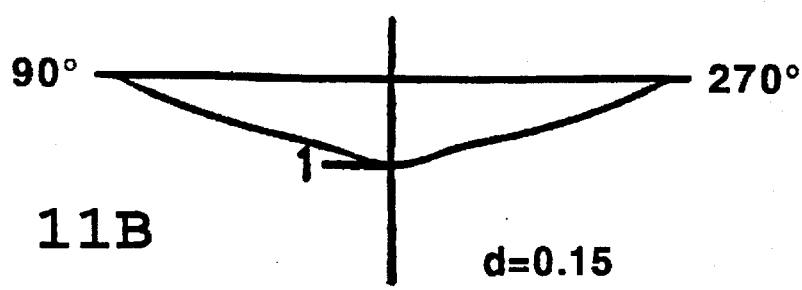
Figure 11C:
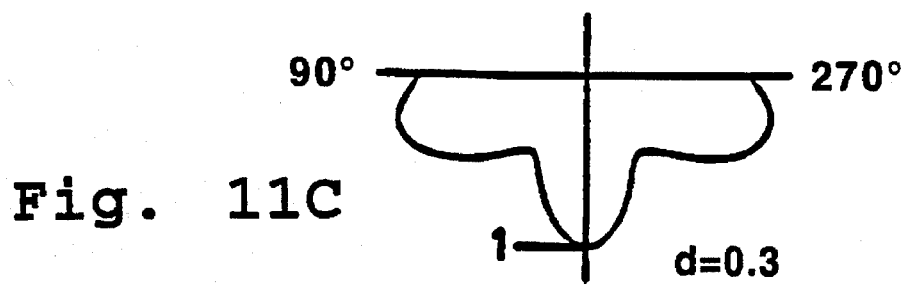
Figure 11D:
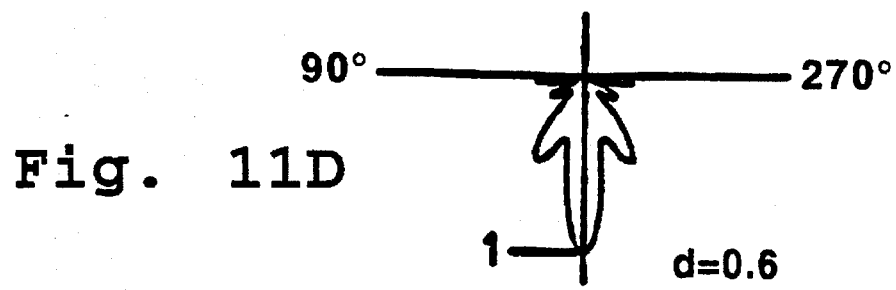
Figure 11E:
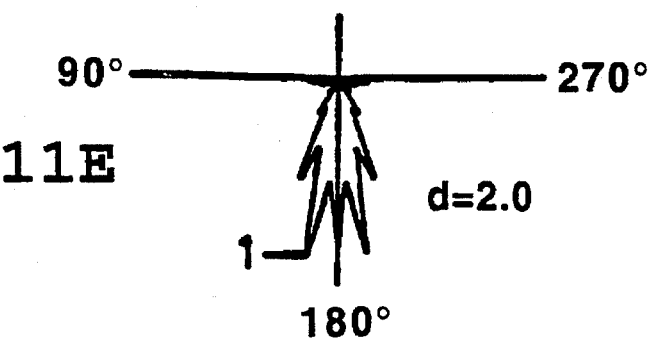

FIGS. 7A–7C show (schematically) an example of a possible standard diffuse reflectance curve RSII1 with two examples for possible measurement curves MHO, and FIG. 8 shows the difference or distortion curves resulting from each of them.

In corresponding advance measurements with the same device a matrix of such distortion curves was prepared and each field of the matrix was assigned to a covered volume V (see FIG. 6). That matrix is not shown here.

In this manner the volume can be determined and in turn used as a correction factor for the previously determined values of the concentration and oxygenation.

Figure 9:
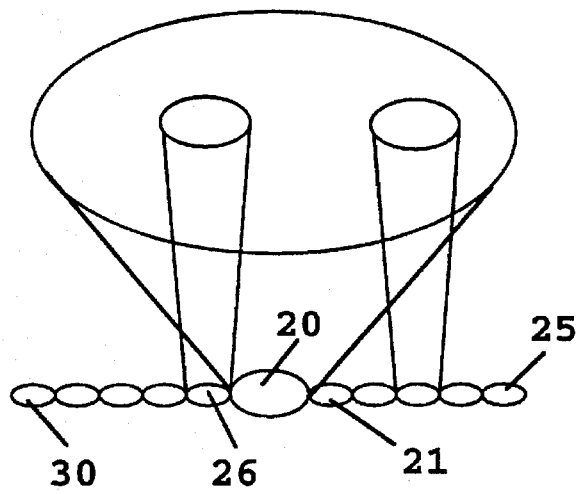
FIG. 9: Schematically, a device for determining the variation of the size of tissue particles.

With a light-guide arrangement shown in FIG. 9 and its use in a special process, the invention also makes it possible to determine the variation of particle sizes in the tissue. This determination is of special practical significance. For example, it can be used to ascertain a size variation of the mitochondria. A preferred embodiment of the device is shown schematically in FIG. 9.

The device consists of an arrangement of a centrally disposed illuminating light guide 20 with a diameter of about 250 μm and detecting light guides, ca. 70 μm in diameter in the example, disposed along a line. With it one can determine the distribution of the back-scattered light in a cross-section of the back-scattering volume, possibly after factoring out the angle distortion resulting from the given arrangement. Since the distribution and intensity of the light in this back-scattering volume varies distinctly with the particle size, a comparison of the diffuse reflectance values obtained from the different detecting light guides 21 to 30 in the course of time enables one to infer the variation of the particle size.

With the assumption of radially symmetric conditions it is also preferred, rather than providing one or two light guides, each at a particular distance (and thus (cone) angle), instead to provide a circle of light guides with a radius equal to the distance. In that way, it is possible to determine the received light power associated with a particular distance, which can be made feasible by connecting together the light guides lying on a circle and evaluating them together.

FIG. 10 shows the large variation of the intensity of the back-scattered (180°) light as a function of the particle size (0.1–2 μm). Detection of this variation by monitoring the time variation, especially the relative variation at the different receiving light guides, thus makes possible a reliable monitoring of the variation, e.g., of the size of the mitochondria and thus, e.g., a timely warning of the development of cerebral edemas.

FIG. 11 shows graphically the change in the distribution of the light, which likewise can be used for the evaluation of the relative diffuse reflectances on the individual or pairs or circles of receiving light guides (here: 21 to 30).

Figure 12:
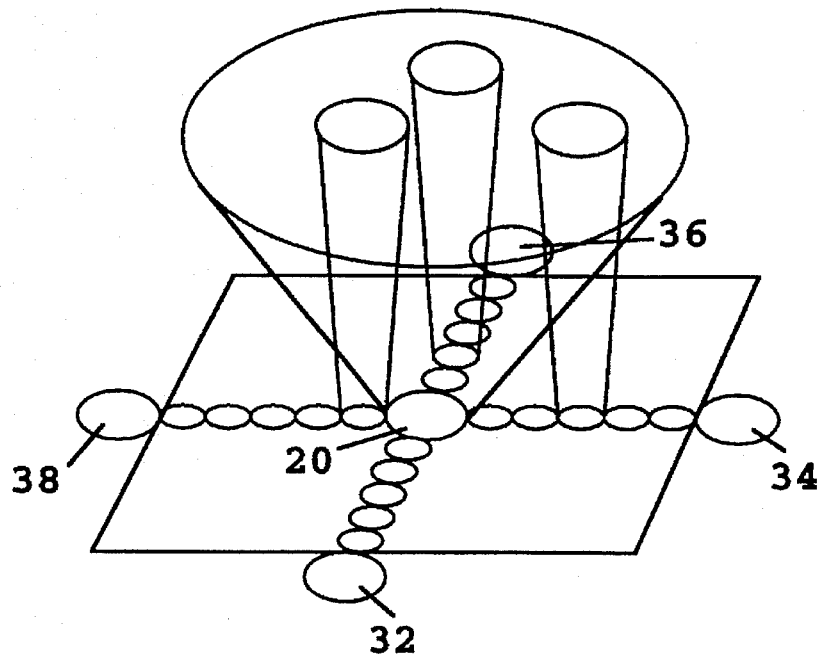
FIG. 12: An arrangement consisting of several illuminating light guides and several receiving light guides, to produce a topography of dye distributions.

In another, especially preferred embodiment, a central illuminating light guide 20 and a field of, for example, 10×10 receiving light guides is provided (see also FIG. 12). This makes possible the measurement of entire topographies of oxygenation and dye distributions.

The items of information coming from the individual light guides are first evaluated individually, as described above in detail for one receiving light guide, and the results then yield a topogram of the Hb concentration, a topogram of the $HbO_2$ concentration and basic diffuse reflectance topograms.

The interrogations of the light guides can be simultaneous, which then makes necessary a corresponding number of the evaluation units described below. However, given the brief period in which a complete spectrum is recorded in both wavelength regions (about 1/100 s), the light guides can also be interrogated in succession, which results in a time difference of about one second, which frequently is acceptable.

The time variation in connection with the angle-dependent corrected spatial diffuse reflectance graph obtained by the arrangement again enables one to reach conclusions about the change of the particle size.

Evaluation of the angle dependence, as concerns both the distance from the illuminating light guide and the circumference of circles around the illuminating light guide, can be used to determine spatial asymmetries.

In another embodiment, which is illustrated concretely in FIG. 12, illuminating light guides 32–38 are also located in the middle of the lateral edges, whereby further information about the scattering behavior in the tissue can be obtained. The volume irradiated by the central light guide and the volumes detectable by each of the detecting light guides are illustrated for specific examples in the drawing.

Figure 13:
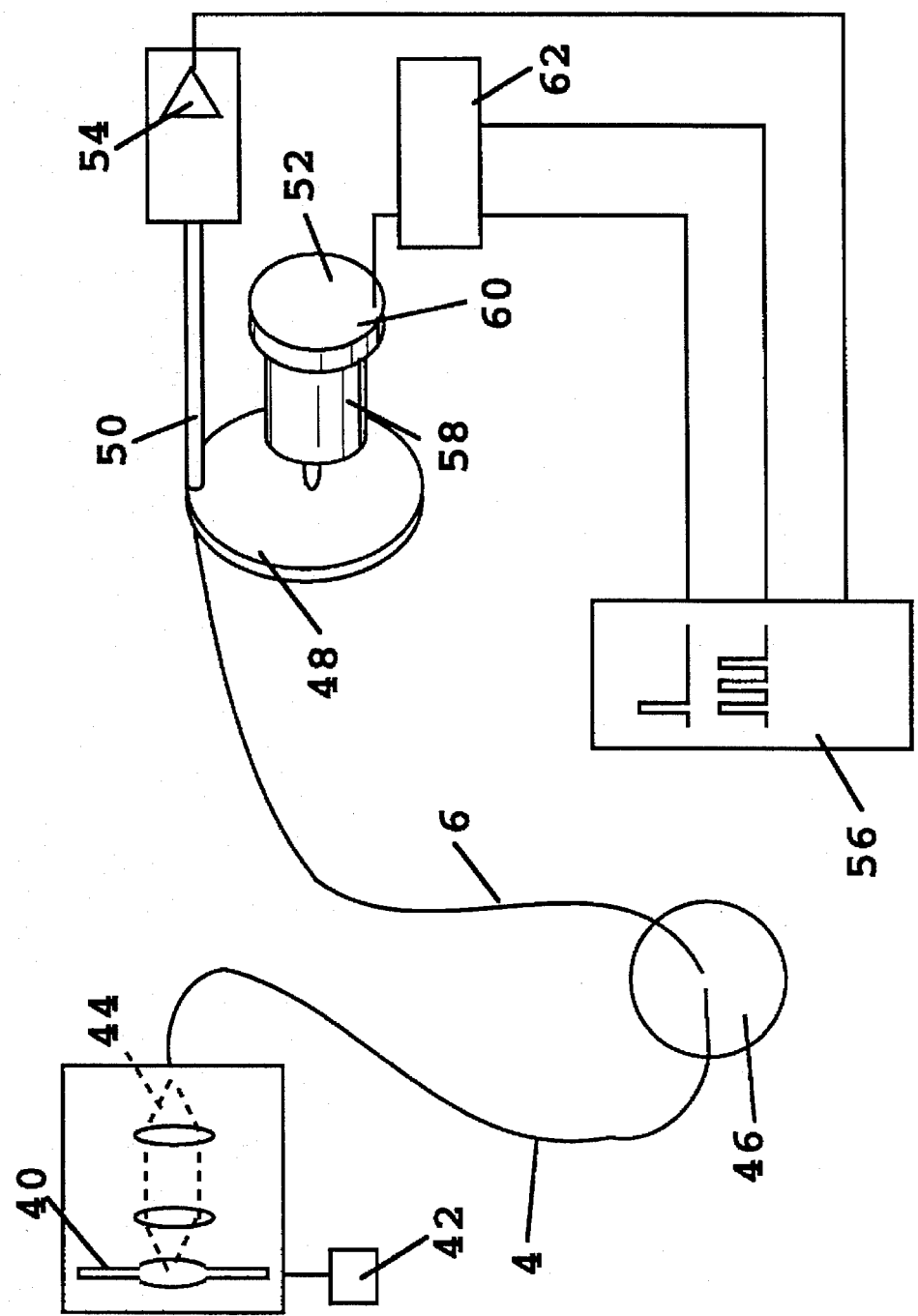
FIG. 13: Schematically, the Erlanger light-guide microspectrophotometer EMPHO which is used for the measurements.

FIG. 13 shows the basic design of the Erlanger light-guide microspectrophotometer. The light of a xenon high-pressure lamp 40 (e.g., XBO 75 W/2, Osram), which is powered by a supply system 42 (stabilized power supply), is irradiated via an optical system 44 into the illuminating light guide 4. The latter is combined with the detecting (receiving) light guide 6 in such a way that the respective end faces lie in one plane and immediately next to one another (not shown in FIG. 13). The pair of light guides (or the arrangement from FIG. 9 or FIG. 12) is then placed on the tissue surface 46. Via the receiving light guide 6 the light reaches an interference graded-density filter disk 48. In the invention, the latter encompasses the wavelength range of from 500 up to 850 nm, in contrast to the interference graded-density filter disks used heretofore for tissue spectrophotometry. It is obvious that then the measurements of the curves MI0 and MHO can occur practically simultaneously and the order depends only on the rotation direction of the filter disk. The light of the wavelength region Just let through by the interference graded-density filter disk 48 (the resolution is about 2 nm) is sent via a light guide 50 to a photomultiplier 52. Via an amplifier system 54 the signal arrives at an analog-to-digital converter 56 and, after digitization, it is sent to a computer (also in 56) for further processing.

As to which wavelength is involved in each instance, that is determined by disposing on the shaft of the motor 58 driving the filter disk 48 a decoder disk 60 and sending the control signals to an EPROM 62. The EPROM 62 converts the control signals into trigger signals for the digitization of the measurement signal by the A/D converter 56. The decoder disk also produces a pulse which marks the beginning of each disk rotation and which initializes the digitization by the A/D converter.

The present process works with absolute values of the diffuse reflectance. Therefore, special attention is paid to the calibration of the entire arrangement.

Figure 14:
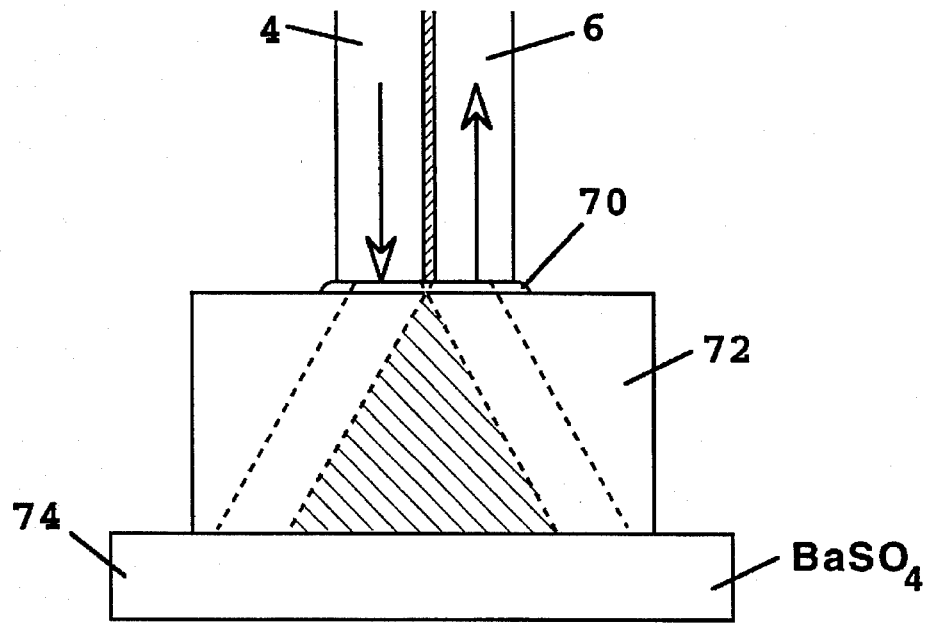
FIG. 14: An arrangement for calibrating the device of FIG. 13.

FIG. 14 shows the device for establishing a white spectrum. The spectral distribution of the light of the xenon arc lamp, the transmission characteristics of the optical elements (lenses, light guides) and the spectral sensitivity of the photomultiplier yield a wavelength-dependent response function for white light. This can be measured by means of the spectrum of a white standard, here $BaSO_4$, using the known device shown in FIG. 14.

In the arrangement used for the measurement, the illuminating (4) and receiving (6) light guides are placed vertically in a drop of immersion fluid 70 (0.9% NaCl) on a glass plate 72. The glass plate provides a fixed distance to the white standard 74. The intersection region 76 of the light cones corresponds to the volume V. To establish the intensity range, a wavelength-dependent dark curve must be stored.

Figure 15:
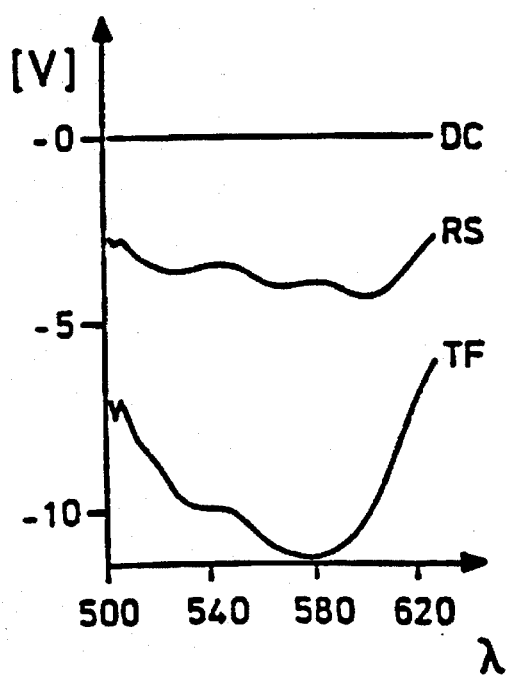
FIG. 15: Curves which show calibration curves and a measured curve.
Figure 16:
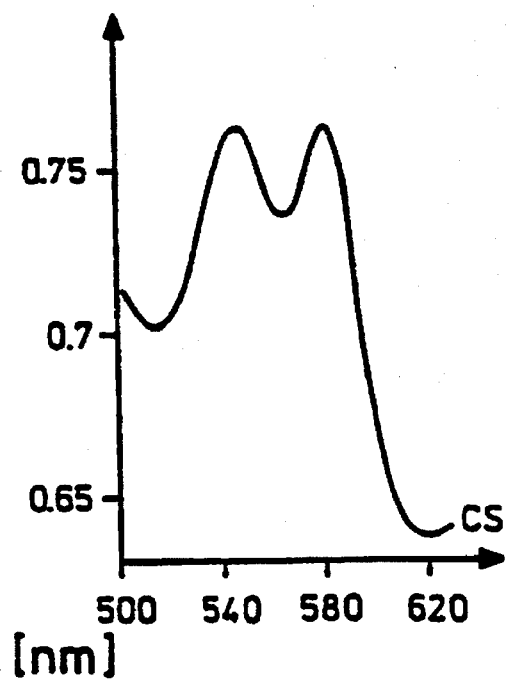
FIG. 16: A measurement curve corrected using the calibration curve.

The correction of the spectrophotometric measurements is performed in four steps. For this, reference is made to FIG. 15 and 16.

1. The recorded measured spectrum RS is subtracted from the dark curve DC.
2. The spectrum of the $BaSO_4$ white standard (BaSt) is also subtracted from the dark curve (DC) (DC−BaSt=TF).
3. The quotient (DC−RS)/(DC−BaSt) yields the corrected spectrum CS (FIG. 16).
4. For the display the corrected spectrum is multiplied by −1.

In order to obtain absolute values of the concentration and because the measurements of the curves MI0 and MII0, on the one hand, and the measurement of the standard basic diffuse reflectance curves and other of the described comparison curves, on the other hand, may be performed at completely different times, an absolute calibration of, for example, the photomultiplier and other light-measuring devices that may be used is especially important. Used for that purpose is a standard light source, preferably in the form of a beta light, in which zinc sulfide or some other radioluminescing substance is excited by radioactive decay products, particularly beta rays of tritium. This is described in more detail in the older German patent application "Normallichtquelle" ("Standard light source") of the same applicant and the same inventors, official file number P 38 16 489.2 33, to which express reference is made.

We claim:

1. A method of noninvasively determining changes in the sizes of selected tissue particles in a tissue in a living animal or human, comprising:
    providing a device which comprises
        (i) a light source,
        (ii) coupled to said light source, an illuminating light guide for radiating light into an animal or human tissue to produce back-scattered light, said light guide having an end which is distal to said light source,
        (iii) at least two receiving light guides having distal ends located at different radial distances from the end of the illuminating light guide, for receiving back-scattered light, wherein the distal ends of said irradiating light guide and receiving light guides terminate in a common plane,
        (iv) evaluating means coupled to each of the receiving light guides, for evaluating, as a function of time, the relative intensities of back-scattered light received by each receiving light guide, to provide a back-scatter profile as a function of time, and
    means for determining, from said profile, a change in size of said tissue particles;
    placing the distal ends of the illuminating and receiving light guides of said device adjacent a target tissue of said animal or human;
    illuminating the tissue with said illuminating light guide under conditions effective to generate back-scattered light from tissue particles in the target tissue;
    measuring the intensities of light received by said receiving light guides using said evaluation means, to obtain a back-scatter profile as a function of time; and
    determining, from said profile, a change in size of said tissue particles.

2. The method of claim 1, wherein said receiving light guides are disposed along a line on both sides of the illuminating light guide.

3. The method of claim 1, wherein said device includes at least two receiving light guides having substantially parallel ends that are equidistant from the illuminating light guide.

* * * * *